(12) United States Patent
Kumar et al.

(10) Patent No.: US 12,421,615 B2
(45) Date of Patent: Sep. 23, 2025

(54) ENGINEERED ELECTRODE FOR ELECTROBIOCATALYSIS AND PROCESS TO CONSTRUCT THE SAME

(71) Applicant: Indian Oil Corporation Limited, Mumbai (IN)

(72) Inventors: Manoj Kumar, Haryana (IN); Prakash Chandra Sahoo, Haryana (IN); Srikanth Sandipam, Haryana (IN); Suresh Kumar Puri, Haryana (IN); Sankara Sri Venkata Ramakumar, Haryana (IN)

(73) Assignee: Indian Oil Corporation Limited, Mumbai (IN)

( * ) Notice: Subject to any disclaimer, the term of this patent is extended or adjusted under 35 U.S.C. 154(b) by 0 days.

(21) Appl. No.: 18/603,491

(22) Filed: Mar. 13, 2024

(65) Prior Publication Data

US 2024/0218537 A1    Jul. 4, 2024

Related U.S. Application Data

(62) Division of application No. 16/668,832, filed on Oct. 30, 2019, now abandoned.

(30) Foreign Application Priority Data

Oct. 30, 2018   (IN) .............................. 201821040950

(51) Int. Cl.
| | |
|---|---|
| *C25B 11/073* | (2021.01) |
| *B82Y 5/00* | (2011.01) |
| *B82Y 15/00* | (2011.01) |
| *B82Y 30/00* | (2011.01) |
| *C12N 1/20* | (2006.01) |
| *C12N 11/02* | (2006.01) |
| *C25B 3/00* | (2021.01) |
| *C25B 11/043* | (2021.01) |
| *H01M 8/16* | (2006.01) |

(52) U.S. Cl.
CPC ............. *C25B 11/073* (2021.01); *C12N 1/20* (2013.01); *C12N 11/02* (2013.01); *C25B 3/00* (2013.01); *C25B 11/043* (2021.01); *H01M 8/16* (2013.01); *B82Y 5/00* (2013.01); *B82Y 15/00* (2013.01); *B82Y 30/00* (2013.01)

(58) Field of Classification Search
CPC . C12N 1/20; C12N 11/02; C25B 3/00; H01M 8/16; B82Y 5/00; B82Y 15/00; B82Y 30/00

See application file for complete search history.

(56) References Cited

U.S. PATENT DOCUMENTS

| 2017/0058409 A1 | 3/2017 | Kumar et al. |
| 2020/0131650 A1 | 4/2020 | Kumar et al. |

FOREIGN PATENT DOCUMENTS

| CN | 107271524 | * 10/2017 |
| EP | 3647434 A1 | 5/2020 |
| JP | 2013239292 | * 11/2013 |

OTHER PUBLICATIONS

CN107271524 machine translation generated in Espacenet. p. 1-10 (Year: 2017).*
Nevin KP et al. Anode Biofilm Transcriptomics Reveals Outer Surface Components Essential for High Density Current Production in Geobacter sulfurreducens Fuel Cells. PLoS One. vol. 4, Issue 5. p. 1-11 (Year: 2009).
Zhu N et al. Improved performance of membrane free single-chamber air-cathode microbial fuel cells with nitric acid and ethylenediamine surface modified activated carbon fiber felt anodes, Bioresource Technology, 102. 422-426 (Year: 2011).
Shukla SK et al. Chitosan-based nanomaterials:, A state-of-the-art review, International Journal of Biological Macromolecules, 59. 46-58 (Year: 2013).
Hu H et al. Biofilm activity and sludge characteristics affected by exogenous N-acyl homoserine lactones in biofilm reactors, Bioresource Technology. 339-347. (Year: 2016).

* cited by examiner

*Primary Examiner* — Paul J Holland
(74) *Attorney, Agent, or Firm* — Blank Rome LLP

(57) ABSTRACT

The present disclosure provides a ready-to-use bio-electrode stable for long term storage and a process of constructing the same. The process for construction of bio-electrode for electro-biocatalysis comprising of: selection of an electro-active bacteria; enrichment of said electro-active bacteria in a nutrient rich medium; separation of said electro-active bacterial cells from said nutrient rich medium; selection of an electrode material; surface modification of said electrode material; layering the surface modified electrode material with conductive material; layering the surface modified electrode material with an electro-active bacterial cells along with biofilm inducing agents and stabilizing agents; conditioning the electro-active bacterial cells layered electrode; incubating the electrode obtained with an immobilizing agent along with conductive material; and conditioning the electrode with micronutrients to obtain a bio-electrode.

9 Claims, 2 Drawing Sheets

ENGINEERED ELECTRODE FOR ELECTROBIOCATALYSIS AND PROCESS TO CONSTRUCT THE SAME

CROSS-REFERENCE TO RELATED APPLICATIONS

Figure 1:
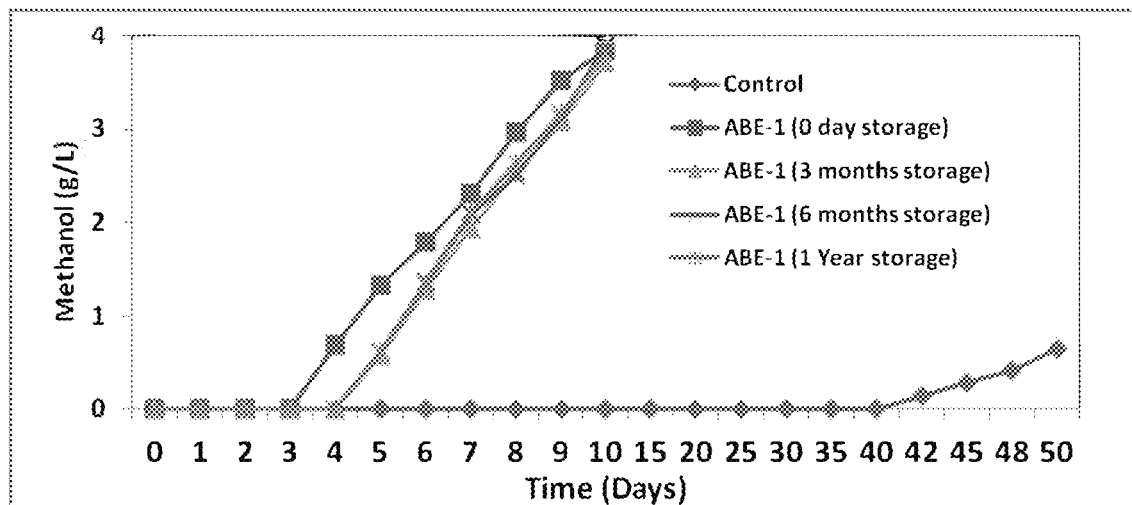

The present patent application is a divisional of U.S. patent application Ser. No. 16/668,832, filed on Oct. 30, 2019, entitled "ENGINEERED ELECTRODE FOR ELECTROBIOCATALYSIS AND PROCESS TO CONSTRUCT THE SAME", claims priority from the Indian Patent application 201821040950, filed on Oct. 30, 2018. Both applications are incorporated by reference herein in their entirety and for all purposes.

FIELD OF THE INVENTION

The present disclosure relates to the field of bio-electrochemical system. In particular, the present disclosure provides a ready-to-use bio-electrode stable for long term storage and a process of constructing the same.

BACKGROUND OF THE INVENTION

Bio-electrochemical System (BES) relies on the interaction of electro-active microbes with electrodes. Electro-active microbes form a biofilm on the electrode and directly or indirectly transfer electrons to convert chemical energy to electricity or vice versa using inorganic/organic source of carbon. The natural formation of an electro-active biofilm, with stable current consumption/production entails prolonged conditioning periods, as long as several weeks to months, depending upon the nature of electrodes, and bacterial physiology. This long duration for production of biofilm makes the BES less attractive. Moreover, a system like microbial electro-synthesis where $CO_2$ is converted to organic chemicals, suffers from stability of biofilm on the electrode. This delicate biofilm gets disrupted many times and takes a long time to regenerate.

Hence, there is need to develop a process for rapid biofilm development on the electrode and make them ready for use as when required by making them stable for long term storage under optimum conditions. Moreover, the nature and structure of the biofilm should be unchanged.

There are some studies where mature biofilm formed naturally is immobilized on a conductive material to make it stable for a long term usage. For such immobilization, various immobilizing agents like agar, pectin, alginate, gelatin and silica gel have been used.

EP0751046A1 describes an electrode structure capable of realizing an electrode array which allows each of the electrodes to be individually controlled while allowing them to be densely arranged and placed in a living body. It describes an electrode control circuit electrically connected to an electrode body is fixed to a rear portion of the electrode body within a front-viewed contour of the electrode body. This electrode control circuit may be contained in a recess formed in the rear portion of the electrode body, or it may be fixed to the back face of the electrode body. Conversely, an electrically conductive material layer covering the electrode control circuit may be used as the electrode body. A plurality of such bio-electrodes may be arranged in a two-dimensional form (array) on a substrate or connected by a connection line including an electrical wire. Such configurations allow the bio-electrodes to be densely arranged.

US20120138485A1 discloses a method for monitoring the metabolic state of an organelle in the presence of a potential organelle modulating agent. In this invention, a first organelle-modified bio-electrode is provided that is electrically coupled to a second electrode of opposite polarity in a circuit. The first bio-electrode is contacted with an aqueous carrier containing a biologically acceptable electrolyte and an effective amount of a potential organelle modulating agent and an effective amount of an organelle substrate. The substrate is reacted at the bio-electrode to form an ionic product that is released into the aqueous carrier-containing electrolyte to thereby provide a current at the second electrode when the circuit is closed. A metabolic flux data set is obtained during the reaction and is compared to a control metabolic flux data set obtained under the same conditions in the absence of the organelle modulating agent, thereby determining the metabolic state of the organelle.

US20170296079A1 describes an electrically conductive material including a base and a conductive polymer applied uniformly to the base's surface and having a reduced resistance value.

U.S. Pat. No. 8,005,526B2 describes bio-electrodes having enhanced biocompatible and biomimetic features. Methods of making and using the bio-electrodes are further provided. A biologically integrated bio-electrode device and method for detecting electronic signals using a bio-electrode comprising a first electrically conductive substrate and a biological component. The bio-electrode also comprises a conductive polymer electrically coupling the first electrically conductive substrate and the biological component to define a bio-electrode. The bio-electrode can transmit or receive an electrical signal between the electrically conductive substrate and the biological component and conductive polymer.

U.S. Pat. No. 6,599,714B1 describes that bacteria are incubated to form a biofilm on projections by providing a flow of liquid growth medium across projections, the direction of the flow of liquid being repeatedly changed, and an assay made of the resulting biofilm. Bacteria are incubated to form a biofilm on projections arranged in rows, with several projections in each row, while providing a flow of liquid growth medium across each row of projections, and an assay made of the resulting biofilm. Sensitivity of the biofilm to antibacterial reagent may be determined by treating the projections with antibacterial reagent before carrying out the assay, by treating each row of projections with a different antibacterial reagent, and each of the projections in a row with a different concentration of antibacterial reagent.

WO/2014/022734A1 describes a synthetic biofilm in which microorganisms are immobilized or embedded within a matrix that is gas-permeable and water-permeable. The synthetic biofilm can be coated on or embedded as a layer within a supporting substrate.

JP2012030196A describes a biofilm forming method capable of forming a long-term biofilm in water such as natural world rivers, lakes and reservoirs while receiving force such as waves and water current without the problem of durability, and a biofilm forming material for use in the method. The biofilm forming method arranges in water a composite material including a matrix material of an organic material and a carbon fiber which is embedded in the matrix material and at least part of which is exposed on the matrix material surface.

WO/1999/041354A1 describes a methodology for controlled biofilm formation. In this invention, a natural biofilm inoculum is used to form a simulated natural biofilm on retrievable slides in an annular reactor. The monitor protocol in the annular reactor subjects the bacterial consortia of the simulated natural biofilm to simulated environmental conditions. The invention simulated natural biofilm on a slide surface has utility for the testing of formulated product activity for inhibition or removal of the simulated natural biofilm, thereby providing a reliable indicator of the relative activity of the products under natural environmental conditions.

U.S. Pat. No. 9,837,677B2 describes methods, systems, and devices for generating electricity from an effluent source. In the presence of electrogenic bacteria and substrate, an electro-active biofilm is produced which possesses bio-conductive capacity for efficiently producing an electric current.

WO2010044983A2 describes a method for preparing a microbial fuel cell, wherein the method includes: (i) inoculating an anodic liquid medium in contact with an anode of the microbial fuel cell with one or more types of microorganisms capable of functioning by an exoelectrogenic mechanism; (ii) establishing a biofilm of the microorganisms on and/or within the anode along with a substantial absence of planktonic forms of the microorganisms by substantial removal of the planktonic microorganisms during forced flow and recirculation conditions of the anodic liquid medium; and (iii) subjecting the microorganisms of the biofilm to a growth stage by incorporating one or more carbon containing nutritive compounds in the anodic liquid medium during biofilm formation or after biofilm formation on the anode has been established.

U.S. Pat. No. 9,673,471B2 describes method for the production of a biofilm at the surface of an electrode in a liquid medium containing bacteria and a substrate for growth of the bacteria.

WO2012149487A1 describes methods and devices for the detection of corrosive biofilms and microbiologically influenced (MIC) corrosion rates are based upon the electrogenicity of the biofilms.

US20110236769A1 describes a microbial fuel cell comprising an anode compartment wherein the microbial biofilm forms on the electrode.

Marta Estevez-Canales in a paper titled Silica immobilization of *Geobacter sulfurreducens* for constructing ready-to-use artificial bio-electrodes published in Microbial Biotechnology (2018) 11(1), 39-49 describes constructing ready-to-use artificial bio-electrodes by immobilizing *Geobacter sulfurreducens* cells in composite materials associating silica gel and carbon felt fibers.

Adachi, M et al in their study "A Novel mediator-polymer-modified anode for microbial fuel cells", Chem Commun 10:2055-2057 (2008) describes a high-performance anode system based on a combination of mediator-polymer-modified graphite felt and bacteria capable of reducing extracellular materials shows significant potential for practical use in microbial fuel cells (MFCs).

Katuri, K et al through their work "Three-dimensional micro-channeled electrodes in flow-through configuration for bioanode formation and current generation", Energy Environ Sci 4:4201-4760 (2011) fabricated a three-dimensional micro-channeled nano-composite electrodes fabricated by ice-segregation induced self-assembly of chitosan-dispersed multiwall carbon nanotubes are shown to provide a scaffold for growth of electro-active bacteria for use as acetate-oxidizing bioanodes in bio-electrochemical systems. The hierarchical structure provides a conductive surface area available for *G. sulfurreducens* colonization, with a flow through configuration along the electrode providing a substrate for bacterial colonization and bio-electrochemical processes.

Luckarift, H. R. et al in their study "Facile fabrication of scalable, hierarchically structured polymer/carbon architectures for bioelectrodes", ACS App. Mater Interfaces 4:2082-2087 (2012) describes a method for fabrication of conductive electrode materials with hierarchical structure from porous polymer/carbon composite materials and demonstrated it for application in microbial fuel cell (MFC) anodes. Bacterial cells were immobilized via chemical vapor deposition (CVD) of silica to create an engineered biofilm that exhibits efficient bio-electrocatalysis of a simple-carbon fuel in a MFC.

Sizemore, S. R. et al in their study "Immobilization of whole cells by chemical vapor deposition of silica", Methods Mol Biol 80:4331-4340 (2013) describes a process for effective entrapment of whole bacterial cells onto solid-phase materials that can significantly improve bioprocessing and other biotechnology applications.

Srikanth, S., et al in their work "Electrochemical characterization of *Geobacter sulfurreducens* cells immobilized on graphite paper electrodes", Biotechnology Bioeng 99:1065-1073 (2008) describes a procedure for immobilization of *Geobacter sulfurreducens* on graphite electrodes that allow routine, repeatable electrochemical analysis of cell-electrode interactions. It was found that the ability of washed *G. sulfurreducens* cells produce electrical current that was consistent with the external surface of this bacterium possessing a pathway linking oxidative metabolism to extracellular electron transfer.

Yu, Y.-Y., et al in their work "Conductive artificial biofilm dramatically enhances bioelectricity production in *Shewanella*-inoculated microbial fuel cells", Chem Commun 47:12825-12827 (2011) describes a new strategy of electrogen immobilization developed to construct a conductive artificial biofilm (CAB) on an anode of a microbial fuel cell (MFC). The MFCs equipped with an optimized CAB exhibited an eleven fold increase in power output compared with natural biofilms.

The techniques described in the art require a very long duration (around 3-5 weeks) to make a biofilm on the electrode which is also unstable and subsequently it is immobilized, this as such does not reduce the duration in making effective electro-active biofilm. The present disclosure overcomes the problems associated with the prior-arts and discloses an engineered bio-electrode for electro-biocatalysis and a process to construct the same. This ready to use bio-electrode with a biofilm can be constructed in a few hours (8-24 hours) and is stable for long term storage under optimum conditions with nature and structure of the biofilm remaining unchanged for prolonged applications. Further, such bio-electrode can be modulated to get selective product profile in bio-electrochemical process.

SUMMARY OF THE INVENTION

The present application provides a bio-electrode for electro-biocatalysis, wherein the bio-electrode comprises of electro-active bacteria layered and immobilized on the modified surface of the electrode with an immobilizing agent and conductive material.

In one of the aspect the bio-electrode comprises of an electro-active bacteria selected from the group consisting of *Cupriavidus nector Ralstonia eutropha* DSMZ 428, *Geobacter hydrogenophilus* H-2 DSM 13691, *Methanobacterium palustre* DSMZ 3108, *Geobacter metallireducens*

GS-15 DSMZ 7210, *Geobacter lovleyi* DSMZ 17278, *Geobacter sulfurrenducens* DSMZ 12127, *Shewanella putrefaciens* DSMZ 9471, *Shewanella putrefaciens* DSMZ 6067, *Shewanella putrefaciens* DSMZ 1818, *Acetobac\terium woodi* DSM 1030, *Morella thermocetica* DSM 21394, *Clostridium aceticum* DSMZ 1496, *Clostridium ljungdahlii* DSM 13528, *Sporomusa sphaeroides* DSM 2875, *Sporomusa silvacetica* DSM 10669, *Cupriavidus nectar* DSM 529, Sporomosa ovate DSM 2662.

In one of the aspect the bio-electrode comprises of an electro-active bacteria selected from the group consisting of *Enterobacter aeronenes* MTCC 25016, *Serratia* sp. MTCC 25017, *Citrobacteer intermedius* MTCC 25018, *Pseudomonas aeruginosa* MTCC 25019, *Shewanella* sp. MTCC 25020, *Seudomonas stutzeri* MTCC 25027 or combinations thereof.

In one of the aspect the bio-electrode comprises of an electrode made of material selected from the group consisting of carbon cloth, stainless steel, flat graphite, flat copper, flat nickel, flat stainless steel, copper coated melamine foam, electron carbon fiber mat, carbonized corrugated card-board structures, graphite felt, activated carbon cloth, brush like anode made from carbon fibers, porous Ti4O7 foam prepared by ice-templating, stainless steel felt, fluidized activated carbon particles, single activated carbon particles placed in an anode chamber, porous stainless steel filter membrane, buckypaper, carbon microfiber paper, carbon nano-fiber mat, poly(aniline-co-2,4-diaminnophenol) nanowire network on a carbon plate, polyaniline nanowire network a carbon plate, composite of PPy/anthraquinone-2, 6-disulfonic disodium salt on carbon felt, compositer of MWCNTs and SnO2 on a glassy carbon with PTFE binder, composite of polyaniline/mesoporous tungsten trioxide, graphite rods, graphite fiber brushes, graphite granules, stainless steel mesh, carbon felt, graphite granules, carbon cloth modified with reduced graphene oxide/tetraethylene pentamine, reticulated vitreous carbon, reticulated vitreous carbon modified with MWCNTs, stainless steel plate or a combination thereof.

In one of the aspect the immobilizing agent used in the bio-electrode is selected from the group consisting of pectin, carboxymethylcellulose, propylene glycol, sodium carboxymethylcellulose, polyethylene glycol, hydroxyethylcellulose, alphacyclodextrin, locust bean gum or combinations thereof.

In one of the aspect the conducting material used in the bio-electrode is selected from the group consisting of polymer poly(pyrrole)s (PPY), polycarbazoles, polyindoles, polyazepines, polyanilines (PANI) or combinations thereof.

In one of the aspect the bio-electrode has a shelf life of at least 2 years.

In another aspect the present application provides a process for construction of bio-electrode for electro-biocatalysis, comprising steps of: (a) selection of an electro-active bacteria; (b) enrichment of said electro-active bacteria selected in step (a) in a nutrient rich medium; (c) separation of said electro-active bacterial cells obtained in step (b) from said nutrient rich medium; (d) selection of an electrode material; (e) surface modification of said electrode material selected in step (d); (f) layering the surface modified electrode material obtained in step (e) with conductive material and drying for 1-4 hours; (g) layering the surface modified electrode material obtained in step (f) with an electro-active bacterial cells obtained in step (c) along with biofilm inducing agents and stabilizing agents; (h) conditioning the electro-active bacterial cells layered electrode obtained in step (g); (i) incubating the electrode obtained in step (h) with an immobilizing agent along with conductive material for 2-3 hours; and (j) conditioning the electrode obtained in step (i) with micronutrients to obtain a bio-electrode.

In one of the aspect the process for construction of bio-electrode for electro-biocatalysis comprises use of electro-active bacteria selected from group consisting of *Cupriavidus nector Ralstonia eutropha* DSMZ 428, *Geobacter hydrogenophilus* H-2 DSM 13691, *Methanobacterium palustre* DSMZ 3108, *Geobacter metallireducens* GS-15 DSMZ 7210, *Geobacter lovleyi* DSMZ 17278, *Geobacter sulfurrenducens* DSMZ 12127, *Shewanella putrefaciens* DSMZ 9471, *Shewanella putrefaciens* DSMZ 6067, *Shewanella putrefaciens* DSMZ 1818, *Acetobac\terium woodi* DSM 1030, *Morella thermocetica* DSM 21394, *Clostridium aceticum* DSMZ 1496, *Clostridium ljungdahlii* DSM 13528, *Sporomusa sphaeroides* DSM 2875, *Sporomusa silvacetica* DSM 10669, *Cupriavidus nectar* DSM 529, Sporomosa ovate DSM 2662, *Enterobacter aeronenes* MTCC 25016, *Serratia* sp. MTCC 25017, *Citrobacteer intermedius* MTCC 25018, *Pseudomonas aeruginosa* MTCC 25019, *Shewanella* sp. MTCC 25020, *Seudomonas stutzeri* MTCC 25027 or combinations thereof.

In one of the aspect the process for construction of bio-electrode for electro-biocatalysis comprises use of nutrient rich medium consisting of yeast extract, peptone, mineral salts, vitamins and combinations thereof.

In one of the aspect the process for construction of bio-electrode for electro-biocatalysis comprises use of nutrient rich medium consisting of mineral salts are selected from the group consisting of NaHCO3, NH4Cl, NaH2PO4H2O, KCl, C6H5FeO7 or combinations thereof.

In one of the aspect the process for construction of bio-electrode for electro-biocatalysis comprises use of electrode material selected from the group consisting of carbon cloth, stainless steel, flat graphite, flat copper, flat nickel, flat stainless steel, copper coated melamine foam, electron carbon fiber mat, carbonized corrugated card-board structures, graphite felt, activated carbon cloth, brush like anode made from carbon fibers, porous Ti4O7 foam prepared by ice-templating, stainless steel felt, fluidized activated carbon particles, single activated carbon particles placed in an anode chamber, porous stainless steel filter membrane, buckypaper, carbon microfiber paper, carbon nano-fiber mat, poly(aniline-co-2,4-diaminnophenol) nanowire network on a carbon plate, polyaniline nanowire network a carbon plate, composite of PPy/anthraquinone-2,6-disulfonic disodium salt on carbon felt, compositer of MWCNTs and SnO2 on a glassy carbon with PTFE binder, composite of polyaniline/mesoporous tungsten trioxide, graphite rods, graphite fiber brushes, graphite granules, stainless steel mesh, carbon felt, graphite granules, carbon cloth modified with reduced graphene oxide/tetraethylene pentamine, reticulated vitreous carbon, reticulated vitreous carbon modified with MWCNTs, stainless steel plate or a combination thereof.

In one of the aspect the process for construction of bio-electrode for electro-biocatalysis comprises of surface modification conducted by a treatment with agents selected from the group consisting of acid, base, heat, microwave, ultrasonic or combinations thereof.

In one of the aspect the process for construction of bio-electrode for electro-biocatalysis comprises of layering conducted by procedures selected from a group consisting of mechanical layering, spraying, and dipping.

In one of the aspect the process for construction of bio-electrode for electro-biocatalysis comprises use of stabilizing agents selected from the group consisting of norepinephrine, dopamine, alginate, polyglucosamine, colanic acid, cellulose, emulsan, chitosan, dextran, curdlan, kefiran, lentinan, pullulan or combinations thereof, and wherein inducing agents are selected from the group consisting of N-Butyryl-DL-homocysteine thiolactone, N-Butyryl-DL-homoserine lactone, N-(p-Coumaroyl)-L-homoserine lactone, N-Decanoyl-DL-homoserine lactone, N-Dodecanoyl-DL-homoserine lactone, cis-2-Dodecenoic acid, N-Heptanoyl-DL-homoserine lactone, 2-Heptyl-3-hydroxy-4(1H)-quinolone, N-Hexanoyl-DL-homoserine lactone, N—[(RS)-3-Hydroxybutyryl]-L-homoserine lactone, N-(3-Hydroxydodecanoyl)-DL-homoserine lactone, N-(3-Hydroxytetradecanoyl)-DL-homoserine lactone, N-(β-Ketocaproyl)-L-homoserine lactone, N-(β-Ketocaproyl)-DL-homoserine lactone, cis-11-Methyl-2-dodecenoic acid, N-Octanoyl-DL-homoserine lactone, N-(3-Oxododecanoyl)-L-homoserine lactone, N-(3-Oxooctanoyl)-DL-homoserine lactone, N-(3-Oxooctanoyl)-L-homoserine lactone, N-(3-Oxotetradecanoyl)-L-homoserine lactone, N-Tetradecanoyl-DL-homoserine lactone and a combination thereof.

In one of the aspect the process for construction of bio-electrode for electro-biocatalysis comprises use of immobilizing agent selected from the group consisting of pectin, carboxymethylcellulose, propylene glycol, sodium carboxymethylcellulose, polyethylene glycol, hydroxyethylcellulose, alphacyclodextrin, locust bean gum or combinations thereof.

In one of the aspect the process for construction of bio-electrode for electro-biocatalysis comprises use of conductive material selected from the group consisting of polymer poly(pyrrole)s (PPY), polycarbazoles, polyindoles, polyazepines, polyanilines (PANI) or combinations thereof.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING FIGURES

The following figures form part of the present specification and are included to further illustrate aspects of the present disclosure. The disclosure may be better understood by reference to the figures in combination with the detailed description of the specific embodiments presented herein.

FIG. 1 depicts the graphical representation of electrochemical analysis of bio-electrode constructed by process described in Example 1 and its comparison in four phases, viz immediately after preparation, after 3 months of storage, after 6 months of storage and after 1 year of storage with the control electrode.

Figure 2:
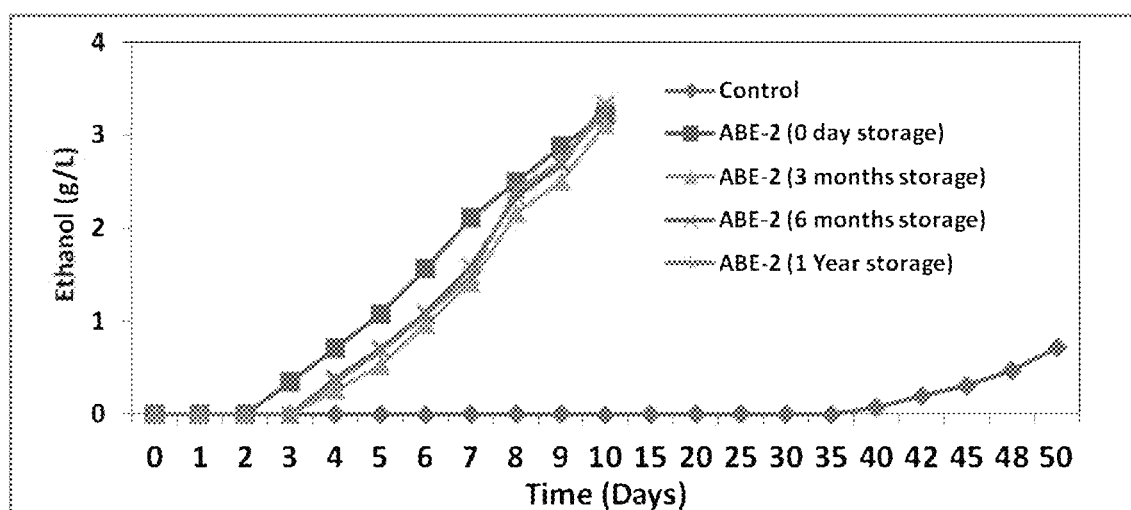

FIG. 2 depicts the graphical representation of electrochemical analysis of bio-electrode constructed by process described in Example 2 and its comparison in four phases, viz immediately after preparation, after 3 months of storage, after 6 months of storage and after 1 year of storage with the control electrode.

Figure 3:
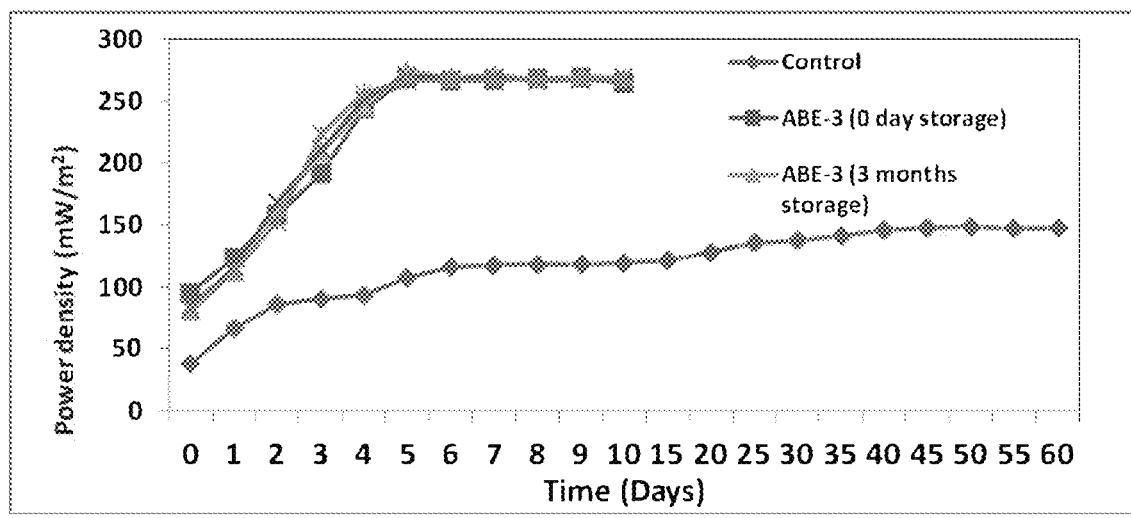

FIG. 3 depicts the graphical representation of electrochemical analysis of bio-electrode constructed by process described in Example 3 and its comparison in four phases, viz immediately after preparation, after 3 months of storage, after 6 months of storage and after 1 year of storage with the control electrode.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features of the process and the product referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products and methods are clearly within the scope of the disclosure, as described herein.

In an embodiment of the present disclosure, there is provided a bio-electrode for electro-biocatalysis, wherein the bio-electrode comprises: electro-active bacteria layered and immobilized on the modified surface of the electrode with an immobilizing agent and conductive material.

In an another embodiment the bio-electrode disclosed in present application comprises of an electro-active bacteria selected from the group consisting of *Cupriavidus nector Ralstonia eutropha* DSMZ 428, *Geobacter hydrogenophilus* H-2 DSM 13691, *Methanobacterium palustre* DSMZ 3108, *Geobacter metallireducens* GS-15 DSMZ 7210, *Geobacter lovleyi* DSMZ 17278, *Geobacter sulfurreducens* DSMZ 12127, *Shewanella putrefaciens* DSMZ 9471, *Shewanella putrefaciens* DSMZ 6067, *Shewanella putrefaciens* DSMZ 1818, *Acetobac\terium woodi* DSM 1030, *Morella thermocetica* DSM 21394, *Clostridium aceticum* DSMZ 1496, *Clostridium ljungdahlii* DSM 13528, *Sporomusa sphaeroides* DSM 2875, *Sporomusa silvacetica* DSM 10669, *Cupriavidus nectar* DSM 529, Sporomosa ovate DSM 2662.

In an another embodiment the bio-electrode disclosed in present application comprises of an electro-active bacteria selected from the group consisting of *Enterobacter aerogenes* MTCC 25016, *Serratia* sp. MTCC 25017, *Citrobacter intermedius* MTCC 25018, *Pseudomonas aeruginosa* MTCC 25019, *Shewanella* sp. MTCC 25020, *Pseudomonas stutzeri* MTCC 25027 or combinations thereof. The microbial strains namely *Enterobacter aerogenes* MTCC 25016, *Serratia* sp. MTCC 25017, *Citrobacter intermedius* MTCC 25018, *Pseudomonas aeruginosa* MTCC 25019, *Shewanella* sp. MTCC 25020 were deposited at Microbial Type Culture Collection & Gene Bank (MTCC), Institute of Microbial Technology, Sector 39-A, Chandigarh-160036 on Apr. 9, 2015. Further, *Pseudomonas stutzeri* MTCC 25027 was deposited at MTCC, Chandigarh on Apr. 20, 2015.

In an another embodiment the bio-electrode disclosed in present application comprises of an electrode made of material selected from the group consisting of carbon cloth, stainless steel, flat graphite, flat copper, flat nickel, flat stainless steel, copper coated melamine foam, electron carbon fiber mat, carbonized corrugated card-board structures, graphite felt, activated carbon cloth, brush like anode made from carbon fibers, porous Ti4O7 foam prepared by ice-templating, stainless steel felt, fluidized activated carbon particles, single activated carbon particles placed in an anode chamber, porous stainless steel filter membrane, buckypaper, carbon microfiber paper, carbon nano-fiber mat, poly(aniline-co-2,4-diaminnophenol) nanowire network on a carbon plate, polyaniline nanowire network a carbon plate, composite of PPy/anthraquinone-2,6-disulfonic disodium salt on carbon felt, composter of MWCNTs and SnO2 on a glassy carbon with PTFE binder, composite of polyaniline/mesoporous tungsten trioxide, graphite rods, graphite fiber brushes, graphite granules, stainless steel mesh, carbon felt, graphite granules, carbon cloth modified with reduced graphene oxide/tetraethylene pentamine, reticulated vitreous carbon, reticulated vitreous carbon modified with MWCNTs, stainless steel plate or a combination thereof.

In an another embodiment the bio-electrode disclosed in present application comprises use of the immobilizing agent selected from the group consisting of pectin, carboxymethylcellulose, propylene glycol, sodium carboxymethylcellulose, polyethylene glycol, hydroxyethylcellulose, alphacyclodextrin, locust bean gum or combinations thereof.

In an another embodiment the bio-electrode disclosed in present application comprises of conducting material selected from the group consisting of polymer poly(pyrrole)s (PPY), polycarbazoles, polyindoles, polyazepines, polyanilines (PANI) or combinations thereof.

In another embodiment the bio-electrode disclosed in present application has a shelf life of at least 2 years.

In another embodiment the bio-electrode disclosed in present application has a shelf life of at least 3 years.

In an embodiment of the present disclosure, there is provided a process of construction of bio-electrode, wherein the process comprises: (a) selection of an electro-active bacteria; (b) enrichment of the electro-active bacteria selected in step (a) in a nutrient rich medium; (c) separation of the electro-active bacterial cells obtained in step (b) from the nutrient rich medium; (d) selection of an electrode material; (e) surface modification of the electrode material selected in step (d); (f) layering with surface modified electrode material obtained in step (e) with conductive material and drying for 1-4 hours; (g) layering the surface modified electrode material obtained in step (f) with an electro-active bacterial cells obtained in step (c) along with biofilm inducing agents and stabilizing agents; (h) conditioning the electro-active bacteria layered electrode obtained in step (g) for 6-8 hrs; (i) incubating the electrode obtained in step (h) with an immobilizing agent along with conductive material, wherein immobilizing agent is allowed to settle for 2-3 hours; and (j) conditioning the electrode obtained in step (i) with micronutrients to obtain a bio-electrode; wherein the bio-electrode can be stored for more than 2-3 years.

In an embodiment of the present disclosure, there is provided a process of construction of bio-electrode as described herein, wherein the electro-active bacteria in step (a) is selected from the group consisting of *Clostridium ljungdahlii*, *Clostridium beijerinckii Clostridium acetobutylicum Acetobacterium woodii*, *Sporomusa ovate*, *Schewanella Oneidensis*, *Geobacter sulfurreducens*, *Pseudomonas aeruginosa* or combinations thereof.

In an embodiment of the present disclosure, there is provided a process of construction of bio-electrode as described herein, the organism may be fungi, bacteria, yeast.

In an embodiment of the present disclosure, there is provided a process of construction of bio-electrode as described herein, the organism may be any electro-active fungi, bacteria, yeast.

In an embodiment of the present disclosure, there is provided a process of construction of bio-electrode as described herein, wherein the electroactive bacteria in step (a) is selected from the group consisting of *Cupriavidus nector Ralstonia eutropha* DSMZ 428, *Geobacter hydrogenophilus* H-2 DSM 13691, *Methanobacterium palustre* DSMZ 3108, *Geobacter metallireducens* GS-15 DSMZ 7210, *Geobacter lovleyi* DSMZ 17278, *Geobacter sulfurrenducens* DSMZ 12127, *Shewanella putrefaciens* DSMZ 9471, *Shewanella putrefaciens* DSMZ 6067, *Shewanella putrefaciens* DSMZ 1818, *Acetobac\terium woodi* DSM 1030, *Morella thermocetica* DSM 21394, *Clostridium aceticum* DSMZ 1496, *Clostridium ljungdahlii* DSM 13528, *Sporomusa sphaeroides* DSM 2875, *Sporomusa silvacetica* DSM 10669, *Cupriavidus nectar* DSM 529, Sporomosa ovate DSM 2662.

In an embodiment of the present disclosure, there is provided a process of construction of bio-electrode as described herein, wherein the electroactive bacteria in step (a) is selected from the group consisting of *Enterobacter aeronenes* MTCC 25016, *Serratia* sp. MTCC 25017, *Citrobacteer intermedius* MTCC 25018, *Pseudomonas aeruginosa* MTCC 25019, *Shewanella* sp. MTCC 25020, *Seudomonas stutzeri* MTCC 25027 or combinations thereof.

In an embodiment of the present disclosure, there is provided a process of construction of bio-electrode as described herein, wherein the nutrient rich medium consists of yeast extract, peptone, mineral salts and vitamins and combinations thereof and wherein mineral salts are selected from the group consisting of $NaHCO_3$, $NH_4Cl$, $NaH_2PO_4H_2O$, $KCl$, $C_6H_5FeO_7$ or combinations thereof.

In an embodiment of the present disclosure, there is provided a process of construction of bio-electrode as described herein, wherein the electrode material is selected from the group consisting of carbon cloth, stainless steel, flat graphite, flat copper, flat nickel, flat stainless steel, copper coated melamine foam, electron carbon fiber mat, carbonized corrugated card-board structures, graphite felt, activated carbon cloth, brush like anode made from carbon fibers, porous Ti4O7 foam prepared by ice-templating, stainless steel felt, fluidized activated carbon particles, single activated carbon particles placed in an anode chamber, porous stainless steel filter membrane, buckypaper, carbon microfiber paper, carbon nano-fiber mat, poly(aniline-co-2, 4-diaminnophenol) nanowire network on a carbon plate, polyaniline nanowire network a carbon plate, composite of PPy/anthraquinone-2,6-disulfonic disodium salt on carbon felt, composite of MWCNTs and SnO2 on a glassy carbon with PTFE binder, composite of polyaniline/mesoporous tungsten trioxide, graphite rods, graphite fiber brushes, graphite granules, stainless steel mesh, carbon felt, graphite granules, carbon cloth modified with reduced graphene oxide/tetraethylene pentamine, reticulated vitreous carbon, reticulated vitreous carbon modified with MWCNTs, stainless steel plate or combinations thereof.

In an embodiment of the present disclosure, there is provided a process of construction of bio-electrode as described herein, wherein the surface modification is conducted by treatment with agents selected from the group consisting of acid, base, heat, microwave, ultrasonic or combinations thereof.

In an embodiment of the present disclosure, there is provided a process of construction of bio-electrode as described herein, wherein the layering in step (f) is conducted by procedures selected from a group consisting of mechanical layering, spraying, and dipping.

In an embodiment of the present disclosure, there is provided a process of construction of bio-electrode as described herein, wherein the biofilm stabilizing agents are selected from the group consisting of norepinephrine, dopamine, alginate, polyglucosamine, colanic acid, cellulose, emulsan, chitosan, dextran, curdlan, kefiran, lentinan, pullulan or combinations thereof and wherein inducing agents are selected from the group consisting of N-Butyryl-DL-homocysteine thiolactone, N-Butyryl-DL-homoserine lactone, N-(p-Coumaroyl)-L-homoserine lactone, N-Decanoyl-DL-homoserine lactone, N-Dodecanoyl-DL-homoserine lactone, cis-2-Dodecenoic acid, N-Heptanoyl-DL-homoserine lactone, 2-Heptyl-3-hydroxy-4(1H)-quinolone, N-Hexanoyl-DL-homoserine lactone, N—[(RS)-3-Hydroxybutyryl]-L-homoserine lactone, N-(3-Hydroxydodecanoyl)-DL-homoserine lactone, N-(3-Hydroxytetradecanoyl)-DL-homoserine lactone, N-(β-Ketocaproyl)-L-homoserine lactone, N-(β-Ketocaproyl)-DL-homoserine lactone, cis-11-Methyl-2-dodecenoic acid, N-Octanoyl-DL-homoserine lactone, N-(3-Oxododecanoyl)-L-homoserine lactone, N-(3-Oxooctanoyl)-DL-homoserine lactone, N-(3-Oxooctanoyl)-L-homoserine lactone, N-(3-Oxotetradecanoyl)-L-homoserine lactone, N-Tetradecanoyl-DL-homoserine lactone and a combination thereof.

In an embodiment of the present disclosure, there is provided a process of construction of bio-electrode as described herein, wherein the immobilizing agents are selected from the group consisting of pectin, carboxymethylcellulose, propylene glycol, sodium carboxymethylcellulose, polyethylene glycol, hydroxyethylcellulose, alphacyclodextrin, locust bean gum or combinations thereof.

In an embodiment of the present disclosure, there is provided a process of construction of bio-electrode as described herein, wherein the conducting material is selected from the group consisting of polymer poly(pyrrole)s (PPY), polycarbazoles, polyindoles, polyazepines, polyanilines (PANI) or combinations thereof.

In an embodiment of the present disclosure, there is provided a process of construction of bio-electrode as described herein, wherein the biofilm on the electrode can be produced in a few hours and can be used several times without affecting its activity.

In an embodiment of the present disclosure, there is provided a method for rapid development of stable biofilm on an electrode and the method of construction of the bio-electrode.

In an embodiment of the present disclosure, there is provided a process to rapidly develop biofilm on an electrode and make them ready for use as when required by making them stable for long term storage under optimum conditions.

In an embodiment of the present disclosure, there is provided a process to construct bio-electrodes which can be modulated to get selective product profile in bio-electrochemical process.

In an embodiment of the present disclosure, there is provided a method of developing biofilm on an electrode comprising of the following steps
  (a) selection of electro-active bacteria (EAB);
  (b) enrichment of the EAB in suitable nutrient rich media;
  (c) separation of EAB cells from media;
  (d) selection of suitable electrode material;
  (e) surface modification of electrode material based on type microbes and targeted product;
  (f) layering of known concentration of the EAB on the modified surface under designated conditions along with biofilm stabilizing agents;
  (g) allowing the bacteria layered electrode for conditioning (6-8 hours) to form a synergistic interaction between the electrode and EAB layer;
  (h) applying the immobilizing agent along with conductive material in a concentration required to get the electron transfer for particular product slate;
  (i) conditioning of the EAB layered electrode during immobilization with micronutrients;
  (j) allow the immobilizing agent to settle for 2-3 hours at optimum condition; and
  (k) application of artificial bio-electrode in a BES as bio-anode or bio-cathode.

In an embodiment of the present disclosure, there is provided a process of construction of bio-electrode as described herein, wherein the concentration of bacteria and $CO_2$ should be controlled for product yield and selectivity.

In an embodiment of the present disclosure, there is provided a process of construction of bio-electrode as described herein, wherein the bio-electrode can be used in a bio-electrochemical system as a bio-anode or a bio-cathode.

In an embodiment of the present disclosure, there is provided a process of construction of bio-electrode as described herein, wherein the bio-electrode is capable of being stored at optimum conditions for more than 2-3 years with or without intermittent use.

In an embodiment of the present disclosure, there is provided a process of construction of bio-electrode as described herein, wherein the electro-active bacteria in step (a) may include but not limited to aerobic, anaerobic, microaerophilic, thermophilic, alkalophilic, psychrophilic or a combination thereof.

In an embodiment of the present disclosure, there is provided a process of construction of bio-electrode as described herein, wherein the electro-active bacteria include, chemoautotrophic bacteria, heterotrophic bacteria, homoacetogenic bacteria which can work in synergistic interaction with each other.

In an embodiment of the present disclosure, there is provided a process of construction of bio-electrode as described herein, wherein the electro-active bacteria that can be used in the present disclosure include but not limited to *Geobacter anodireducens, G. argillaceus, G. bemidjiensis, G. bremensis, G. chapellei, G. daltonii, G. grbiciae, G. sulfurreducens, G. thiogenes, G. toluenoxydans, G. uraniireducens, Schewanella abyssi, S. aestuarii, S. algae, S. algidipiscicola, S. amazonensis, S. aquimarina, S. arctica, S. litorisediminis, S. livingstonensis, S. loihica, S. mangrove, S. marina, S. marinintestina, S. marisflavi, S. morhuae, S. olleyana, S. oneidensis, S. piezotolerans, S. pacifica, S. pealeana, S. piezotolerans, S. pneumatophori, S. profunda, S. psychrophila, S. putrefaciens, S. sairae, S. schegeliana, S. sediminis, S. seohaensis, S. spongiae, S. surugensis, S. upenei, S. vesiculosa, S. violacea, S. waksmanii, S. woodyi, S. xiamenensis, Pseudomonas aeruginosa, P. alcaligenes, P. anguilliseptica, P. argentinensis, P. borbori, P. citronellolis, P. flavescens, P. mendocina, P. nitroreducens, P. oleovorans, P. pseudoalcaligenes, P. resinovorans, P. straminea, P. balearica, P. luteola, P. stutzeri, Sporomusa ovate, Clostridium ljungdahlii, Sporomusa acidovorans, cyanobacterium Synechocystis, Pelotomaculum thermopropionicum, Megasphaera hexanoica, Megasphaera hominis, Megasphaera cerevisiae, Megasphaera elsdenii, Megasphaera micronuciformis, Megasphaera paucivorans, Megasphaera sueciensis, M. cerevisiae, Anaeroglobus geminates, Clostridium acetobutylicum, Clostridium butyricum, Clostridium diolis, Clostridium beijerinckii, Clostridium acidisoli, Clostridium aciditolerans, Clostridium acidurici, Clostridium aerotolerans, Clostridium cadaveris, Clostridium caenicola, Clostridium caminithermale, Clostridium carboxidivorans, Clostridium carnis, Clostridium cavendishii, Clostridium celatum, Clostridium celerecrescens, Clostridium cellobioparum, Clostridium cellulofermentans, Clostridium cellulolyticum, Clostridium cellulosi, Clostridium cellulovorans, D. acrylicus, D. aerotolerans, D. aespoeensis, D. africanus, D. alaskensis, D. alcoholivorans, D. alkalitolerans, D. aminophilus, D. arcticus, D. baarsii, D. baculatus, D. bastinii, D. biadhensis, D. bizertensis, D. burkinensis, D. butyratiphilus, D. capillatus, D. carbinolicus, D. carbinoliphilus, D. cuneatus, D. dechloracetivorans, D. desulfuricans, D. ferrireducens, D. frigidus, D. fructosivorans, D. furfuralis, D. gabonensis, D. giganteus, D. gigas, D. gracilis, D. halophilus, D. hydrothermalis, D. idahonensis, D. indonesiensis, D. inopinatus, D. intestinalis, D. legallii, D. alitoralis, D. longreachensis, D. longus, D. magneticus, D. marinus, D. marinisediminis, D. marrakechensis, D. mexicanus, D. multispirans, D. oceani, D. oxamicus, D. oxyclinae, D. paquesii, D. piezophilus, D. pigra, D. portus, D. profundus, D. psychrotolerans, D. putealis, D. salixigens, D. sapovorans, D. senezii, D. simplex, D. sulfodismutans, D. termitidis, D. thermophilus, D. tunisiensis, D. vietnamensis, D. vulgaris, D. zosterae, Klebsiella granulomatis, Klebsiella oxytoca, Klebsiella pneumonia, Klebsiella terrigena, Klebsiella variicola, Bacillus subtilis, Zymomonas mobilis, Zymomonas anaerobia, Propionibacterium acidipropionici, Propionibacterium acnes, Propionibacterium australiense, Propionibacterium avidum, Propionibacterium cyclohexanicum, Propionibacterium damnosum, Propionibacterium freudenreichii, Propionibacterium granulosum, Propionibacterium jensenii, Propionibacterium lymphophilum, Propionibacterium microaerophilu, Propionibacterium namnetense, Propionibacterium olivae, Propionibacterium propionicus, Propionibacterium thoenii, Acetobacterium woodii, Sporomusa acidovorans, cyanobacterium Synechocystis, Pelotomaculum thermopropionicum, Megasphaera hexanoica, Megasphaera hominis, Megasphaera cerevisiae, Megasphaera elsdenii, Megasphaera micronuciformis, Megasphaera paucivorans, Megasphaera sueciensis, M. cerevisiae, Anaeroglobus geminates* etc.

In an embodiment of the present disclosure, there is provided a process of construction of bio-electrode as described herein, wherein the nutrient rich medium for growing the electro-active bacteria includes following as g/L (NaCl2, 10; NH4CL, 1; K2HPO4, 0.3; KH2PO4, 0.3; MgCl2, 0.2; CaCl2.2H2O, 0.1; KCl, 0.1; MnO4.7H2O, 0.01; ZnSO4.7H2O, 0.05; H3BO3, 0.01; N(CH2COOH), 4.5; CaCl2.2H2O, 0.01; Na2MoO4, 0.01; CoCl2.6H2O, 0.2; ALK(SO4)2, 0.01; MgCl2.6H2O, 00.2; FeCl3, 0.1; CuCl2.6H2O, 0.05); yeast extract 0.5%; peptone 0.25% and vitamin solution (g/L, riboflavin, 0.025; citric acid, 0.02; folic acid, 0.01; para-amino benzoic acid, 0.01) along with acetic acid as C-source.

In an embodiment of the present disclosure, there is provided a process of construction of bio-electrode as described herein, wherein, the electro-active bacteria is grown under electric circuit of about 3 V cell potential for 2-20 hours.

In an embodiment of the present disclosure, there is provided a process of construction of bio-electrode as described herein, wherein the separation of bacterial cells from medium is carried out after the OD of 6.0 is reached.

In an embodiment of the present disclosure, there is provided a process of construction of bio-electrode as described herein, wherein the electrode material may be made from any conducting material biocompatible with microbes.

In an embodiment the present disclosure, there is provided a process of construction of bio-electrode as described herein, wherein the electrode material may be selected from conducting material including but not limited to carbon cloth, stainless steel, flat graphite, flat copper, flat nickel, flat stainless steel, copper coated melamine foam, electron carbon fiber mat, carbonized corrugated card-board structures, graphite felt, activated carbon cloth, brush like anode made from carbon fibers, porous $Ti_4O_7$ foam prepared by ice-templating, stainless steel felt, fluidized activated carbon particles, single activated carbon particles placed in an anode chamber, porous stainless steel filter membrane, buckypaper, carbon microfiber paper, carbon nano-fiber mat, poly(aniline-co-2,4-diaminnophenol) nanowire network on a carbon plate, polyaniline nanowire network a carbon plate, composite of PPy/anthraquinone-2,6-disulfonic disodium salt on carbon felt, composite of MWCNTs and SnO2 on a glassy carbon with PTFE binder, composite of polyaniline/mesoporous tungsten trioxide, graphite rods, graphite fiber brushes, graphite granules, stainless steel mesh, carbon felt, graphite granules, carbon cloth modified with reduced graphene oxide/tetraethylene pentamine, reticulated vitreous carbon, reticulated vitreous carbon modified with MWCNTs, stainless steel plate or a combination thereof.

In an embodiment of the present disclosure, there is provided a process of construction of bio-electrode as described herein, wherein the surface modification of the electrode is done using acid, base, heat, microwave, ultrasonic or their combination.

In an embodiment of the present disclosure, there is provided a process of construction of bio-electrode as described herein, wherein the surface modification of electrode material is done based on type of microbes and desired product.

In an embodiment of the present disclosure, there is provided a process of construction of bio-electrode as described herein, wherein the electrode materials are selected based on their electron releasing tendency.

In an embodiment of the present disclosure, there is provided a process of construction of bio-electrode as described herein, wherein the electrode materials may contain $CeO_2$, ZnS, $Bi_2S_3$, $NaBiO_3$, $Ga_2O_3$, $g-C_3N_4$, $Cu_2O$, $La_2Ti_2O_7$, $ZnGa_2O_4$, $MCo_2O_4$ (M=Ni, Zn or Mn), C, N-co-doped $Na_2TiO_3$, N-doped ZnO, Zn-doped $Ga_2O_3$, Ni—Al LDH, Ni—Al 4:1, Zn3Ga/CO LDH, 3D hierarchical $SrTiO_3$, $CaTiO_3$, $SrTiO_3$, $KNbO3$, $KTaO_3$ nanoflake, $NaTaO_3$, $BaZrO_3$, $NaBiO_3$, $LaPO_4$, $Bi2S_3$, $CdIn2S_4$, $ZnIn2S_4$, ZnTe, CoTe, carbon dots, S-doped $g-C_3N_4$, Ti-MCM-41, SiC, CdS/Co—ZIF-9, $Cu-TiO2-ZSM-5$ or a combination thereof.

In an embodiment of the present disclosure, there is provided a process of construction of bio-electrode as described herein, wherein a known concentration of the bacterial cells is applied on the surface modified electrode under sterile anaerobic/aerobic conditions along with the molecules which initiate bio-film formation and stabilize the biofilm on the electrode.

In an embodiment of the present disclosure, there is provided a process of construction of bio-electrode as described herein, wherein biofilm initiators may include but are not limited to N-Butyryl-DL-homocysteine thiolactone, N-Butyryl-DL-homoserine lactone, N-(p-Coumaroyl)-L-homoserine lactone, N-Decanoyl-DL-homoserine lactone, N-Dodecanoyl-DL-homoserine lactone, cis-2-Dodecenoic acid, N-Heptanoyl-DL-homoserine lactone, 2-Heptyl-3-hydroxy-4(1H)-quinolone, N-Hexanoyl-DL-homoserine lactone, N—[(RS)-3-Hydroxybutyryl]-L-homoserine lactone, N-(3-Hydroxydodecanoyl)-DL-homoserine lactone, N-(3-Hydroxytetradecanoyl)-DL-homoserine lactone, N-(β-Ketocaproyl)-L-homoserine lactone, N-(β-Ketocaproyl)-DL-homoserine lactone, cis-11-Methyl-2-dodecenoic acid, N-Octanoyl-DL-homoserine lactone, N-(3-Oxododecanoyl)-L-homoserine lactone, N-(3-Oxooctanoyl)-DL-homoserine lactone, N-(3-Oxooctanoyl)-L-homoserine lactone, N-(3-Oxotetradecanoyl)-L-homoserine lactone, N-Tetradecanoyl-DL-homoserine lactone and a combination thereof.

In an embodiment of the present disclosure, there is provided a process of construction of bio-electrode as described herein, wherein the electro-active microbes can be applied on the electrode by mechanical layering, spraying, dipping the electrode.

In an embodiment of the present disclosure, there is provided a process of construction of bio-electrode as described herein, wherein the biofilm stabilizer is applied in a particular concentration.

In an embodiment of the present disclosure, there is provided a process of construction of bio-electrode as described herein, wherein examples of biofilm stabilizing agents may include but are not limited to Norepinephrine, dopamine, Alginate, polyglucosamine, colanic acid, cellulose, emulsan, chitosan, dextran, curdlan, kefiran, Lentinan, pullulan and a combination thereof.

In an embodiment of the present disclosure, there is provided a process of construction of bio-electrode as described herein, wherein the electro-active microbes are allowed to form biofilm on the electrode for 2-4 hours.

In an embodiment of the present disclosure, there is provided a process of construction of bio-electrode as described herein, wherein the immobilizing agent along with conductive material is applied in a concentration required to get the electron transfer for a particular product slate.

In an embodiment of the present disclosure, there is provided a process of construction of bio-electrode as described herein, wherein the immobilizing agent may be organic or inorganic and formed from pectin, carboxymethylcellulose and propylene glycol; modified carboxymethylcellulose (2.3%) and propylene glycol (20%); sodium carboxymethylcellulose, polyethylene glycol and propylene glycol, cationic derivative of hydroxyethylcellulose, alpha-cyclodextrin, and locust bean gum.

In an embodiment of the present disclosure, there is provided a process of construction of bio-electrode as described herein, wherein the immobilizing agent must contain a 2D material such as porous graphene, MWCNT, $gC_3N_4$ or $MoS_2$ along with a conducting polymer poly (pyrrole)s (PPY), polycarbazoles, polyindoles, polyazepines, polyanilines (PANI).

In an embodiment of the present disclosure, there is provided a process of construction of bio-electrode as described herein, wherein the immobilizing agent improves the microstructure or mechanical properties of biofilm through colloidal self-assembly of cells and polymers.

In an embodiment of the present disclosure, there is provided a process of construction of bio-electrode as described herein, wherein the biofilm thickness and cell density can be controlled and have good reproducibility.

Although the subject matter has been described in considerable detail with reference to certain preferred embodiments thereof, other embodiments are possible.

Having described the basic aspects of the present invention, the following non-limiting examples illustrate specific embodiment thereof.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Example 1—Selective Biosynthesis of Methanol Using Artificially Constructed Bio-Electrode Bacterial Culture Three different microbial cultures, viz., *Pseudomonas aeruginosa* MTCC 25019, *Shewanella* sp. MTCC 25020, *Seudomonas stutzeri* MTCC 25027 were grown separately at 30° C. in a medium containing the following mineral salts (per litre): 2.5 g of $NaHCO_3$, 0.25 g of $NH_4Cl$, 0.06 g of $NaH_2PO_4H_2O$, 0.1 g of KCl, 0.024 g of $C_6H_5FeO_7$ (ferric citrate), yeast extract 0.5%; peptone 0.25% 10 ml of a vitamin mix and 10 ml of a trace mineral solution. Anaerobic conditions were achieved by flushing the media with $N_2:CO_2$ (80:20) to remove oxygen and to keep the pH of the bicarbonate buffer at pH 6.8. In log phase microbial culture was centrifuged (8000 rpm) and washed in phosphate buffer.

Then the equal (wet) weight of the microbes were mixed and added into fresh media, allowed for growth and centrifuged again to separate the selective mixed microbial consortia.

Bio-Electrode Construction a) First, the carbon cloth electrode (5 cm) was treated with an inorganic acid in order to make it more hydrophilic, increasing surface oxidation of the material. Carbon cloth was immersed in nitric acid (65%) for 48 hours. Then, the felt was rinsed with bicarbonate buffer (pH 6.8). A gel of 0.25 g Cu nano particle and 0.5 g Polyaniline (PANI) was prepared and applied on the surface of treated carbon cloth by mechanical layering. After drying at room temperature for 2 hours, the 0.2 g (wet) centrifuged mixed microbial consortia of example 1 as developed above was applied on the same electrode using mechanical layering. After 30 minutes, the 50 ml of the 0.1 mM N-Butyryl-DL-homocysteine thiolactone was uniformly added to the adhered microbes to induce biofilm production and dried at room temperature for 45 minutes. Then 0.12 mM Dopamine solution was applied to stabilize the biofilm. Then the electrode was incubated at 30° C. for 2-4 hours to allow the microbes to form biofilm.

b) In a separate 250 ml beaker, 50 mg of porous graphene and 0.52 ml of propylene glycol (2 M), 0.1 ml of TEOS, 0.1 M borax and 1.5 ml of bicarbonate buffer (90 mM) were mixed. An anoxic chamber filled with $N_2$—$CO_2$ (80:20), was used in order to maintain anaerobic conditions, providing an atmosphere of 0-5 parts per million (ppm) using a palladium catalyst and hydrogen gas mix of 5%.

c) Immobilization of biofilm on surface modified electrode of example 1 as obtained above by incubating for 20 minutes in the solution of example 1 as obtained above with continuous bubbling accompanied with a flux of $N_2$—$CO_2$ (80:20) to maintain anoxic conditions inside the bio-electrode.

d) Bio-electrodes after their construction were immersed in the culture media as used for bacterial culture of example 1. After 1 day of incubation at 30° C., the ready to use bio-electrode was evaluated in electrochemical synthesis.

e) The cell concentration was $8.2 \times 10^6$ cfu/cm$^2$ of the electrode with 0.2 microgram of Cu-nano particles/cm of electrode surface.

Electrochemical Analysis and Calculations

Experiment was carried out by using the artificial bio-electrode, prepared as described above in four phases, viz., immediately after preparation, after 3 months of storage, after 6 months of storage and after 1 year of storage. Control operation was carried out using natural biofilm developed on the electrode with conventional methods. Control operation did not show any current consumption till $14^{th}$ day of operation followed by small current consumption which also did not result in any significant product formation. The current consumption is visible after $35^{th}$ day where the acetic acid synthesis was observed and that was followed by methanol production from $42^{nd}$ day of operation. Gradual increment in methanol production was observed thereafter and reached 0.64 g/l by $50^{th}$ day. On the contrary, the artificial bio-electrode of example 1, developed with the same microbes, started the current consumption from day 2 of operation resulting in formic and acetic acid production. Methanol production was observed from day 4 followed by rapid increment in product synthesis at a rate of 0.65 g/l/day (total product) reaching 3.84 g/l in 10 days of operation. After 10 days of operation, the artificial bio-electrode was taken out carefully under anaerobic conditions and preserved at 4° C. for by dipping in media containing PBS added with 1% mineral solution, 0.2% Vitamin solution, 1% bicarbonate and 0.3% formic acid (final pH, 7.4). After 3 months of storage, the artificial bio-electrode was taken out and evaluated in new experiment after keeping overnight in fresh media. This time, the current consumption started a day later compared to the first experiment but after that almost similar results were obtained resulting in synthesis of 3.71 g/l methanol in 10 days. The same method of electrode storage was repeated again and after 3 more months later, the experiment was repeated and obtained the similar results (3.9 g/l in 10 days). Further, the artificial bio-electrode was stored for 6 months and 1 year continuously and evaluated in a similar way. The results obtained were similar to the earlier results (3.81 g/l) indicating the retained capability of the electrode. When the control electrode after 60 days of biofilm growth was stored in similar way as artificial bio electrode of example 1 and was evaluated after 3 months, no current consumption and product synthesis was observed even after 25 days of operation.

Example 2—Selective Biosynthesis of Ethanol Using Artificially Constructed Bioelectrode Bacterial Culture Three different microbial cultures, viz., *Clostridium ljungdahlii* DSM 13528, *Sporomusa silvacetica* DSM 10669, *Cupriavidus nectar* DSM 529, Sporomosa ovate DSM 2662 were grown separately at 30° C. in a medium containing the following mineral salts (per litre): 2.5 g of $NaHCO_3$, 0.25 g of NHCl, 0.06 g of $NaH_2PO_4H_2O$, 0.1 g of KCl, 0.024 g of $C_6H_5FeO_7$ (ferric citrate), 10 ml of a vitamin mix and 10 ml of a trace mineral solution. Anaerobic conditions were achieved by flushing the media with $N_2:CO_2$ (80:20) to remove oxygen and to keep the pH of the bicarbonate buffer at pH 6.8. Each microbial culture was centrifuged (8000 rpm) and washed in phosphate buffer. Then the equal (wet) weight of the microbes were mixed and added into fresh media, allowed for growth and centrifuged again to separate the selective mixed microbial consortia.

Bio-Electrode Construction a) First, the carbon felt electrode (5 cm$^2$) was treated with an inorganic acid in order to make it more hydrophilic, increasing surface oxidation of the material. Carbon cloth was immersed in nitric acid (65%) for 48 hours. Then, the felt was rinsed with bicarbonate buffer (pH 6.8). A gel of 0.25 g $NiCo_2O_4$ nano-particle and 0.5 g Polyaniline (PANI) was prepared and applied on the surface of treated carbon felt by mechanical layering. After drying at room temperature for 2 hours, the 0.2 g (wet) centrifuged mixed microbial consortia of example 2 as developed above was applied on the same electrode using mechanical layering. After 30 minutes, the 50 ml of the 0.1 mM N-(3-Oxotetradecanoyl)-L-homoserine lactone was uniformly added to the adhered microbes to induce biofilm production and dried at room temperature for 45 minutes. Then 0.10 mM Colanic acid solution was applied to stabilize the biofilm. Then the electrode was incubated at 30° C. for 2-4 hours to allow the microbes to form biofilm.

b) In a separate 250 ml beaker, 50 mg of multi walled CNT and 0.52 ml of polyethylene glycol (2 M), 0.1 ml of TEOS, 0.1 M borax and 1.5 ml of bicarbonate buffer (90 mM) were mixed. An anoxic chamber filled with $N_2$—$CO_2$ (80:20), was used in order to maintain anaerobic conditions, providing an atmosphere of 0-5 parts per million (ppm) using a palladium catalyst and hydrogen gas mix of 5%.
c) Immobilization of biofilm on surface modified electrode of example 2 as obtained above by incubating for 20 minutes in the solution of example 2 as obtained above, with continuous bubbling accompanied with a flux of $N_2$—$CO_2$ (80:20) to maintain anoxic conditions inside the bio-electrode.
d) Bio-electrodes after their construction were immersed in the culture media as used for bacterial culture of example 2. After 1 day of incubation at 30° C. the ready to use bio-electrode was evaluated in electrochemical synthesis.

Electrochemical Analysis and Calculations

Another experiment was carried out in similar way as disclosed in Example-1 by using different artificial bio-electrode prepared as described above to re-check the objective. Experiment was carried out in four phases, viz., immediately after preparation, after 3 months of storage, after 6 months of storage and after 1 year of storage. Control operation was carried out using natural biofilm developed on the electrode with conventional methods. Control operation did not show any current consumption till $12^{th}$ day of operation followed by small current consumption which also did not result in any significant product formation. The current consumption was visible after $30^{th}$ day, where the acetic acid synthesis was observed and that was followed by ethanol and production from $42^{nd}$ day of operation. Gradual increment in methanol production was observed thereafter and reached 0.71 g/l by 50 day. On the contrary, the artificial bio-electrode of example 2, developed with the same microbes started current consumption from day 2 of operation resulting in formic and acetic acid production. Methanol production was observed from day 4 followed by rapid increment in product synthesis at a rate of 0.58 g/l/day (total product) reaching 3.21 g/l in 10 days of operation. After 10 days of operation, the artificial bio-electrode was taken out carefully under anaerobic conditions and preserved at 4° C. for by dipping in media containing PBS added with 1% mineral solution, 0.2% Vitamin solution, 1% bicarbonate and 0.3% formic acid (final pH, 7.4). After 3 months of storage, the artificial bio-electrode was taken out and evaluated in new experiment after keeping overnight in fresh media. This time, the current consumption started a day later compared to the first experiment but after that almost similar results were obtained resulting in synthesis of 3.11 g/l ethanol in 10 days. The same method of electrode storage was repeated again and after 3 more months later, the experiment was repeated and obtained the similar results (3.34 g/l in 10 days). Further, the artificial bio-electrode was stored for 6 months and 1 year continuously and evaluated in similar way. The results obtained were similar to the earlier results (3.26 g/l) indicating the retained capability of the electrode. Similar to the Example-1, when the control electrode after 60 days of biofilm growth was stored in similar way as artificial bio-electrode of example 2 and was evaluated after 3 months, no current consumption and product synthesis was observed even after 25 days of operation.

Example-3—Artificially Constructed Bio-Electrode for MFC Application

Bacterial Culture

Three different microbial cultures, viz, *Pseudomonas aeruginosa* MTCC 25019, *Shewanella* sp. MTCC 25020 were grown separately at 30° C. in a medium containing the following mineral salts (per litre): 2.5 g of $NaHCO_3$, 0.25 g of $NHCl$, 0.06 g of $NaH_2PO_4H_2O$, 0.1 g of KCl, 0.024 g of $C_6H_5FeO_7$ (ferric citrate), 10 ml of a vitamin mix and 10 ml of a trace mineral solution. Anaerobic conditions were achieved by flushing the media with $N_2$:$CO_2$ (80:20) to remove oxygen and to keep the pH of the bicarbonate buffer at pH 6.8. When the OD reaches to 6.0, each microbial culture was centrifuged (8000 rpm) and washed in phosphate buffer. Then the equal (wet) weight of the microbes were mixed and added into fresh media, allowed for growth and centrifuged again to separate the selective mixed microbial consortia.

Bio-Electrode Construction a) First, the carbon fiber mat electrode (5 cm²) was treated with an inorganic acid in order to make it more hydrophilic, increasing surface oxidation of the material. Carbon cloth was immersed in nitric acid (65%) for 48 hours. Then, the carbon fiber mat was rinsed with bicarbonate buffer (pH 6.8). A gel of 0.25 g Cu nano particle and 0.5 g Polyaniline (PANI) was prepared and applied on the surface of treated carbon fiber mat by mechanical layering. After drying at room temperature for 2 hours, the 0.2 g (wet) centrifuged mixed microbial consortia of example 3 as developed above was applied on the same electrode using mechanical layering. After 30 minutes, the 50 ml of the 0.1 mM N-Heptanoyl-DL-homoserine lactone was uniformly added to the adhered microbes to induce biofilm production and dried at room temperature for 45 minutes. Then 0.12 mM Kefiran solution was applied to stabilize the biofilm. Then the electrode was incubated at 30° C. for 2-4 hours to allow the microbes to form biofilm.
b) In a separate 250 ml beaker, 50 mg of $MoS_2$ and 0.52 ml of propylene glycol (2 M), 0.1 ml of TEOS, 0.1 M borax and 1.5 ml of bicarbonate buffer (90 mM) were mixed. An anoxic chamber filled with $N_2$—$CO_2$ (80:20), was used in order to maintain anaerobic conditions, providing an atmosphere of 0-5 parts per million (ppm) using a palladium catalyst and hydrogen gas mix of 5%.
c) Immobilization of biofilm on surface modified electrode of example 3 as obtained above by incubating for 20 minutes in the solution of example 3 as obtained above with continuous bubbling accompanied with a flux of $N_2$—$CO_2$ (80:20) to maintain anoxic conditions inside the bio-electrode.
d) Bio-electrodes after their construction were immersed in the culture media as used for bacterial culture of example 3. After 1 day of incubation at 30° C., the ready to use bio-electrode was evaluated in electrochemical synthesis.

Electrochemical Analysis and Calculations

In another experiment, the artificial bio-electrode was prepared to use as bioanode for oxidation of organics present in wastewater. Similar to other examples, present experiment was also carried out in four phases, viz., immediately after preparation, after 3 months of storage, after 6 months of storage and after 1 year of storage. Control operation was carried out using natural biofilm developed on the electrode with conventional methods. Control operation showed little power density of about 38 mW/m² immediately after start-up which increased gradually with time and reached to its maximum by $35^{th}$ day (145±3 mW/m²). This operation resulted in about 95% treatment efficiency with respect to TOC removal after 40 days of operation. On the contrary, the artificial bio-electrode of example 3, developed with the same microbes, has started power generation of about 96 mW/m², immediately after start-up, which increased rapidly on daily basis and reached its maximum by 5$^{th}$ day of operation (265±3 mW/m²). After 10 days of operation, the artificial bio-electrode was taken out carefully under anaerobic conditions and preserved at 4° C. for by dipping in media containing PBS added with 1% mineral solution, 0.2% Vitamin solution, 1% glucose and 0.3% acetic acid (final pH, 7.0). After 3 months of storage, the artificial bio-electrode was taken out and evaluated in a new experiment after keeping overnight in fresh media. This time, the current consumption started at little lower value of 81 mW/m², but reached to similar maximum value of 265±3 mW/m² in 5 days and sustained thereafter. The same method of electrode storage was repeated again and after 3 more months later, the experiment was repeated and obtained the similar results (268±2 mW/m²). Further, the artificial bio-electrode was stored for 6 months continuously and evaluated in similar way. The results obtained were similar to the earlier results (267±3 mW/m²) indicating the retained capability of the electrode. Similar to the other examples, when the control electrode after 60 days of biofilm growth was stored in similar way as artificial bio-electrode of example 3 and was evaluated after 3 months, negligible power generation was observed even after 25 days of operation.

Overall, the present disclosure provides a process of constructing a ready-to-use bio-electrode that can be constructed in a few hours and is stable for long term storage under optimum conditions. The process and methods described in the disclosure ensure efficient electric current between the biofilm and the electrode materials.

We claim:

1. A process for constructing a bio-electrode, the process consisting of:
    selecting an electro-active bacteria from the group consisting of *Enterobacter aerogenes* MTCC 25016, *Serratia* sp. MTCC 25017, *Citrobacter intermedius* MTCC 25018, *Pseudomonas aeruginosa* MTCC 25019, *Shewanella* sp. MTCC 25020, *Pseudomonas stutzeri* MTCC 25027, *Clostridium ljungdahlii* DSM 13528, *Sporomusa silvacetica* DSM 10669, *Cupriavidus* nectar DSM 529, Sporomosa ovate DSM 2662, and combinations thereof;
    enriching the electro-active bacteria in a nutrient rich medium to obtain electro-active bacterial cells;
    separating the electro-active bacterial cells obtained from the nutrient rich medium;
    providing an electrode material;
    surface modifying the electrode material by treating it with an acid and rinsing with a bicarbonate buffer;
    layering the surface modified electrode material with a conductive material and drying for a period of 1-4 hours at room temperature;
    further layering the dried surface modified electrode material with the electro-active bacterial cells, adding a biofilm inducing agent, drying at room temperature for a period of 45 minutes, and applying a stabilizing agent;
    conditioning the electro-active bacterial cells layered surface modified electrode material; and
    incubating the conditioned electro-active bacterial cells layered surface modified electrode material with an immobilizing agent and the conductive material for a period of 2-3 hours at 30° C., and conditioning with micronutrients to obtain the bio-electrode,
    the constructing of the bio-electrode takes a time period of 8 to 24 hours to impart a shelf-life of at least 2-3 years.

2. The process according to claim 1, wherein the nutrient rich medium consists of yeast extract, peptone, mineral salts, vitamins and combinations thereof.

3. The process according to claim 2, wherein the mineral salts are selected from the group consisting of $NaHCO_3$, $NH_4Cl$, $NaH_2PO_4H_2O$, $KCl$, $C_6H_5FeO_7$, and combinations thereof.

4. The process according to claim 1, wherein the electrode material is selected from the group consisting of carbon cloth, stainless steel, flat graphite, flat copper, flat nickel, flat stainless steel, copper coated melamine foam, electron carbon fiber mat, carbonized corrugated card-board structures, graphite felt, activated carbon cloth, brush like anode made from carbon fibers, porous $Ti_4O_7$ foam prepared by ice-templating, stainless steel felt, fluidized activated carbon particles, single activated carbon particles placed in an anode chamber, porous stainless steel filter membrane, buckypaper, carbon microfiber paper, carbon nano-fiber mat, poly(aniline-co-2,4-diaminnophenol) nanowire network on a carbon plate, polyaniline nanowire network a carbon plate, composite of PPy/anthraquinone-2,6-disulfonic disodium salt on carbon felt, composiier of MWCNTs and $SnO_2$ on a glassy carbon with PTFE binder, composite of polyaniline/mesoporous tungsten trioxide, graphite rods, graphite fiber brushes, graphite granules, stainless steel mesh, carbon felt, graphite granules, carbon cloth modified with reduced graphene oxide/tetraethylene pentamine, reticulated vitreous carbon, reticulated vitreous carbon modified with MWCNTs, stainless steel plate, and a combination thereof.

5. The process according to claim 1, wherein the layering is performed by mechanical layering, spraying, or dipping.

6. The process according to claim 1, wherein the stabilizing agent is selected from the group consisting of norepinephrine, dopamine, alginate, polyglucosamine, colanic acid, cellulose, emulsan, chitosan, dextran, curdlan, kefiran, lentinan, pullulan, and combinations thereof.

7. The process according to claim 1, wherein the biofilm inducing agent is selected from the group consisting of N-Butyryl-DL-homocysteine thiolactone, N-Butyryl-DL-homoserine lactone, N-(p-Coumaroyl)-L-homoserine lactone, N-Decanoyl-DL-homoserine lactone, N-Dodecanoyl-DL-homoserine lactone, cis-2-Dodecenoic acid, N-Heptanoyl-DL-homoserine lactone, 2-Heptyl-3-hydroxy-4 (1H)-quinolone, N-Hexanoyl-DL-homoserine lactone, N—[(RS)-3-Hydroxybutyryl]-L-homoserine lactone, N-(3-Hydroxydodecanoyl)-DL-homoserine lactone, N-(3-Hydroxytetradecanoyl)-DL-homoserine lactone, N-(β-Ketocaproyl)-L-homoserine lactone, N-(β-Ketocaproyl)-DL-homoserine lactone, cis-11-Methyl-2-dodecenoic acid, N-Octanoyl-DL-homoserine lactone, N-(3-Oxododecanoyl)-L-homoserine lactone, N-(3-Oxooctanoyl)-DL-homoserine lactone, N-(3-Oxooctanoyl)-L-homoserine lactone, N-(3-Oxotetradecanoyl)-L-homoserine lactone, N-Tetradecanoyl-DL-homoserine lactone, and a combination thereof.

8. The process according to claim 1, wherein the immobilizing agent is selected from the group consisting of pectin, carboxymethylcellulose, propylene glycol, sodium carboxymethylcellulose, polyethylene glycol, hydroxyethylcellulose, alphacyclodextrin, locust bean gum, and combinations thereof.

9. The process according to claim 1, wherein the conductive material is selected from the group consisting of polymer poly(pyrrole)s (PPY), polycarbazoles, polyindoles, polyazepines, polyanilines (PANI), and combinations thereof.

* * * * *